(12) United States Patent
Liu

(10) Patent No.: US 9,271,528 B2
(45) Date of Patent: Mar. 1, 2016

(54) MULTI-FLAVORED ELECTRONIC CIGARETTE

(75) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 575 days.

(21) Appl. No.: 13/704,239

(22) PCT Filed: Aug. 31, 2012

(86) PCT No.: PCT/CN2012/080846
§ 371 (c)(1),
(2), (4) Date: Dec. 13, 2012

(87) PCT Pub. No.: WO2014/032276
PCT Pub. Date: Mar. 6, 2014

(65) Prior Publication Data
US 2014/0060556 A1 Mar. 6, 2014

(51) Int. Cl.
*A24F 47/00* (2006.01)
*A61M 15/06* (2006.01)
*A61M 15/00* (2006.01)
*A61M 11/04* (2006.01)

(52) U.S. Cl.
CPC ............ *A24F 47/008* (2013.01); *A61M 11/042* (2014.02); *A61M 15/0003* (2014.02); *A61M 15/06* (2013.01); *A61M 2205/3653* (2013.01); *A61M 2205/8206* (2013.01)

(58) Field of Classification Search
CPC .. A24F 47/008; A61M 15/0003; A61M 15/06
See application file for complete search history.

(56) References Cited

U.S. PATENT DOCUMENTS

| | | | | |
|---|---|---|---|---|
| 5,060,671 A | * | 10/1991 | Counts | A24F 47/008 128/202.21 |
| 5,093,894 A | * | 3/1992 | Deevi | A24F 47/008 392/390 |
| 5,095,921 A | * | 3/1992 | Losee | A24F 47/008 128/200.19 |
| 5,144,962 A | * | 9/1992 | Counts | A24F 47/008 128/200.14 |
| 5,179,966 A | * | 1/1993 | Losee | A24F 47/008 128/202.21 |
| 5,224,498 A | * | 7/1993 | Deevi | A24F 47/008 128/202.21 |
| 5,249,586 A | * | 10/1993 | Morgan | A24F 47/008 128/200.14 |
| 5,269,327 A | * | 12/1993 | Counts | A24F 47/008 128/200.14 |
| 5,322,075 A | * | 6/1994 | Deevi | H05B 3/44 131/194 |
| 5,353,813 A | * | 10/1994 | Deevi | A24F 47/008 131/194 |
| 5,408,574 A | * | 4/1995 | Deevi | A24F 47/008 128/202.21 |
| 5,505,214 A | * | 4/1996 | Collins | A24F 47/008 128/202.21 |
| 5,894,841 A | * | 4/1999 | Voges | A24F 47/008 128/200.14 |

(Continued)

*Primary Examiner* — Jason L Lazorcik
(74) *Attorney, Agent, or Firm* — Cheng-Ju Chiang

(57) ABSTRACT

This invention relates to a multi-flavored electronic cigarette, including liquid storage components adapted for reserving liquid smoke and heaters adapted for atomizing liquid smoke to smoke, the electronic cigarette being further provided with at least two atomizing chambers therein adapted for allowing a kind of liquid smoke to be atomized therein to become smoke, each atomizing chamber reserving a kind of liquid smoke and provided with one of the heater, the electronic cigarette being further provided with a heater control circuit board therein electrically connected with each heater, a battery electrically connected with the heater control circuit board and a control switch disposed on an outer shell of the electronic cigarette. This kind of multi-flavored electronic cigarette has multiple atomizing chambers, and satisfies the requirement for free choice of one flavor, multi-flavors or a combination of optional flavors.

13 Claims, 4 Drawing Sheets

(56) References Cited

U.S. PATENT DOCUMENTS

| | | | | |
|---|---|---|---|---|
| 6,234,167 B1* | 5/2001 | Cox | A61M 15/0065 | 128/200.14 |
| 6,501,052 B2* | 12/2002 | Cox | A61M 11/041 | 219/483 |
| 6,568,390 B2* | 5/2003 | Nichols | A61M 15/00 | 128/200.14 |
| 7,513,781 B2* | 4/2009 | Galauner | A61M 11/041 | 439/509 |
| 7,540,286 B2* | 6/2009 | Cross | A61M 15/0045 | 128/203.26 |
| 2006/0054165 A1* | 3/2006 | Hughes | A61M 15/009 | 128/200.14 |
| 2007/0068523 A1* | 3/2007 | Fishman | A61M 16/0051 | 128/203.12 |
| 2008/0247892 A1* | 10/2008 | Kawasumi | F04B 43/12 | 417/476 |
| 2011/0011396 A1* | 1/2011 | Fang | A61M 15/06 | 128/202.21 |
| 2011/0303231 A1* | 12/2011 | Li | A24F 47/008 | 131/329 |
| 2012/0048266 A1* | 3/2012 | Alelov | A61M 11/005 | 128/202.21 |
| 2012/0285475 A1* | 11/2012 | Liu | A24F 47/008 | 131/329 |
| 2013/0228191 A1* | 9/2013 | Newton | A24F 47/008 | 131/329 |
| 2014/0000638 A1* | 1/2014 | Sebastian | A24F 47/008 | 131/328 |
| 2014/0060527 A1* | 3/2014 | Liu | A61M 15/06 | 128/202.21 |
| 2014/0190503 A1* | 7/2014 | Li | A61M 15/06 | 131/329 |
| 2014/0261488 A1* | 9/2014 | Tucker | A24F 47/008 | 131/328 |
| 2015/0013702 A1* | 1/2015 | Liu | A24F 47/008 | 131/329 |
| 2015/0020826 A1* | 1/2015 | Liu | A24F 47/008 | 131/329 |
| 2015/0059787 A1* | 3/2015 | Qiu | H05B 3/14 | 131/329 |
| 2015/0083147 A1* | 3/2015 | Schiff | A24F 47/008 | 131/329 |
| 2015/0164145 A1* | 6/2015 | Zhou | A24D 1/002 | 131/329 |

* cited by examiner

MULTI-FLAVORED ELECTRONIC CIGARETTE

CROSS REFERENCE TO RELATED APPLICATIONS

The present application is a 35 U.S.C. §371 National Phase conversion of International (PCT) Patent Application No. PCT/CN2012/080846, filed on Aug. 31, 2012, the disclosure of which is incorporated by reference herein. The PCT International Patent Application was filed in Chinese.

TECHNICAL FIELD

This invention relates to a field of an electronic cigarette, and especially relates to a multi-flavored electronic cigarette.

DESCRIPTION OF BACKGROUND

Current electronic cigarettes generally comprise a liquid storage component for storing liquid smoke and a heater for atomizing the liquid smoke into vapor, and the electronic cigarettes also have one atomizing chamber for the liquid smoke to be atomized therein, while the atomizing chamber generally can only accommodate one flavor of liquid smoke.

The current electronic cigarettes have the follow shortcomings: since only one atomizing chamber is provided for accommodate the liquid smoke, and each atomizing chamber generally can only accommodate one flavor of liquid smoke, which results in that the vapor after atomized through the current electronic cigarettes has single taste, even the liquid smokes with multiple flavors are mixed in one atomizing chamber, all the flavors of the atomized smokes are also mixed together, this cannot satisfy user's requirement for free choice of multi-flavors and a combination of optional flavors.

SUMMARY

An object of the present invention is to provide a multi-flavored electronic cigarette, which has multiple atomizing chambers and satisfies the requirement for free choice of one flavor, multi-flavors or a combination of optional flavors.

To solve the above object, the present invention provides a multi-flavored electronic cigarette, comprising liquid storage components adapted for reserving liquid smoke and heaters adapted for atomizing liquid smoke to smoke, the electronic cigarette being further provided with at least two atomizing chambers therein adapted for allowing a kind of liquid smoke to be atomized therein to become smoke, each atomizing chamber reserving a kind of liquid smoke and provided with one of the heater, the electronic cigarette being further provided with a heater control circuit board therein electrically connected with each heater, a battery electrically connected with the heater control circuit board and a control switch disposed on an outer shell of the electronic cigarette.

Furthermore, the atomizing chambers each are provided with a conduit adapted for supporting the liquid storage components, the liquid storage components are sleeve-shaped, and sleeved around outer portions of the conduits.

Furthermore, the heaters each comprise a heating wire and a liquid guiding component adapted for absorbing liquid smoke and supporting the heating wire, the conduits each form a locking slot extending through a side wall thereof in a radial direction and adapted for mounting the liquid guiding component, opposite ends of the liquid guiding component project the side wall of the conduits and abut against inner sides of the liquid storage components.

Furthermore, the sucking cylinder is further provided with a liquid smoke cup configured for receiving the liquid storage components and the heaters, the at least two atomizing chambers are disposed in the liquid smoke cup.

Furthermore, the liquid smoke cup comprises a cup tube adapted with the inner side of the sucking cylinder and cup holders with ventholes and a lid with ventholes, the lid and the cup holders are disposed at opposite ends of the cup tube, the cup tube is provided with at least two cavities, the lid is inserted into a top end of the cup tube and hermetically connected with a circumference of the top end of the cavities, the cup holders are inserted into a bottom end of the cup tube and hermetically connected with a circumference of the bottom end of the cavities, the lid and the cup holders are corresponded to restrain the opposite ends of the conduit, the lid and the cup holders are corresponded and construct sealed inner chambers served as the atomizing chambers together with side walls of the cavities, the liquid storage component is disposed within the atomizing chambers.

Furthermore, the cavities are cylinder-shaped, the lid comprises a circular main body, positioning posts axially extended from a bottom wall of the main body to restrain the conduits and ventholes axially extended through the position posts and the main body of the lid; correspondingly, the cup holders each comprise a circular main body, a positioning post axially extended from a central portion of a top wall of the main body of the corresponding cup holder to restrain the conduits and a venthole axially extended through the positioning post and the main body of the corresponding cup holder; the positioning posts of the lid and the positioning posts of the cup holders are respectively inserted into opposite ends of the conduits to position the conduits in the atomizing chambers.

Furthermore, the electronic cigarette adopts a split-type structure, and comprises mutually connected sucking rod and a power rod, the sucking rod at its one end is provided with a first connector, correspondingly, the power rod at its one end is provided with a second connector securely engaged with the first connector.

Furthermore, the heater and the liquid smoke cup are disposed within the sucking rod, while the battery and the heater control circuit board are disposed within the power rod; the first connector is provided with a first electrode of the heater and a first insulating sleeve therein, the first electrode of the heater is mounted by means of the first insulating sleeve into the first connector which serves as a second electrode of the heater; the second connector is provided with a first electrode of the battery and a second insulating sleeve therein; the first electrode of the battery is mounted by means of the second insulating sleeve into the second connector which serves as a second electrode of the battery.

Furthermore, the sucking rod and the power rod are connected by fastener, plug or screw.

Furthermore, the electrode cigarette is integrally formed.

Furthermore, the liquid guiding component is made of glass fiber which is capable of absorbing water and reserving water like a sponge or a material having a liquid-absorbent and fluid barrier properties.

Furthermore, the liquid storage components are made of high temperature resistant cotton, fiberglass cotton or thick cotton cloth capable of absorbing water and reserving water like a sponge.

The multi-flavored electronic cigarette of the present invention is provided with at least two atomizing chambers, each atomizing chamber reserves different flavored liquid smoke, and it depends on the requirement to start the control switch to control the heaters in the atomizing chambers to atomize the liquid smoke in the atomizing chambers, it is capable to start the heater in a single atomizing chamber to work, or simultaneously start the heater in all of the atomizing chambers to work, or start the heaters in any combination of optional atomizing chambers, to satisfy the requirement for free choice of one flavor, multi-flavors or a combination of optional flavors.

The embodiments of the present invention will be described in further detail below in conjunction with the accompanying drawings.

DETAILED DESCRIPTION OF THE EMBODIMENTS

Figure 1:
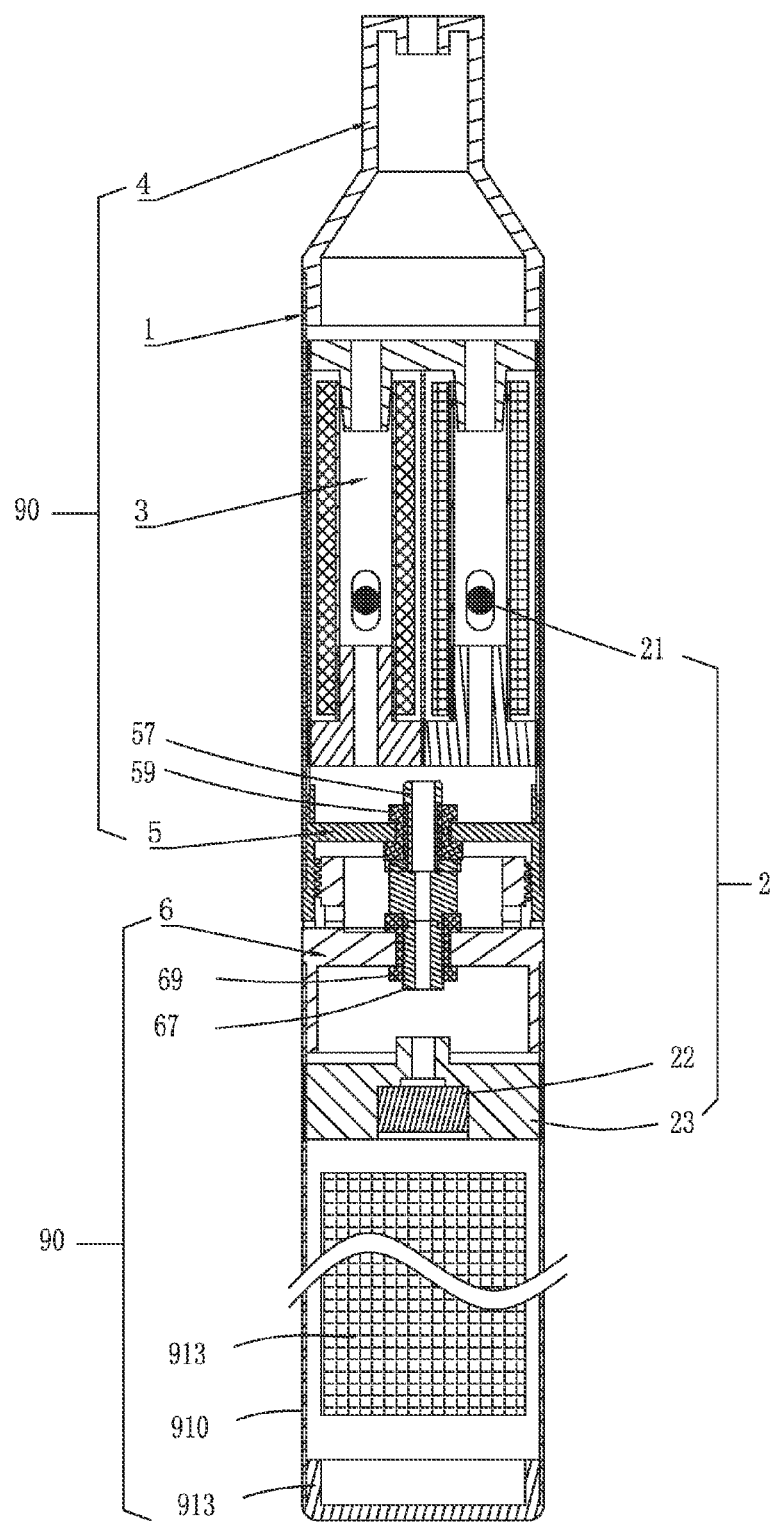
FIG. 1 is a cross-sectional view of a multi-flavored electronic cigarette in accordance with a first embodiment of the present invention.

As shown in FIGS. 1-6, a first embodiment of the present invention provides a multi-flavored electronic cigarette 100, the multi-flavored electronic cigarette 100 is an assembled-type electronic cigarette, which comprises an electronic cigarette sucking rod 90 and a power rod 91, the electronic cigarette sucking rod 90 and the power rod 91 are connected by fastener, plug or screw, and in this embodiment by screw, and the electronic cigarette sucking rod 90 and the power rod 91 are screwed together by a first connector 5 disposed on the sucking rod 90 and a second connector 6 disposed on the power rod 91 described in details hereafter. The directions described in this embodiment are based on the directions shown in FIG. 2.

In the embodiment, the electronic cigarette sucking rod 90 comprises a sucking cylinder 1 with a hollow inner chamber, a heating device 2, a liquid smoke cup 3 configured with multiple atomizing chambers therethrough side by side, a sucking nozzle 4 having a venthole and the first connector 5 for connecting with the power rod 9. The sucking nozzle 4 and the first connector 5 are respectively mounted to opposite ends of the sucking cylinder 1, and the heating device 2 and the liquid smoke cup 3 are disposed within the sucking cylinder.

As shown in FIG. 2 to FIG. 6, the heating device 2 comprises a heater 21, a heater control circuit board 22 and a circuit board positioning seat 23 for positioning the heater control circuit board 22, in the embodiment, the heater 21 is disposed within the electronic cigarette sucking rod 90, while the heater control circuit board 22 and the circuit board positioning seat 23 are disposed within the power rod 91, the heater control circuit board 22 respectively controls multiple heaters 21 to work, and can simultaneously start them or any combination of several of them. In the embodiment two heaters 21 are provided.

Figure 3:
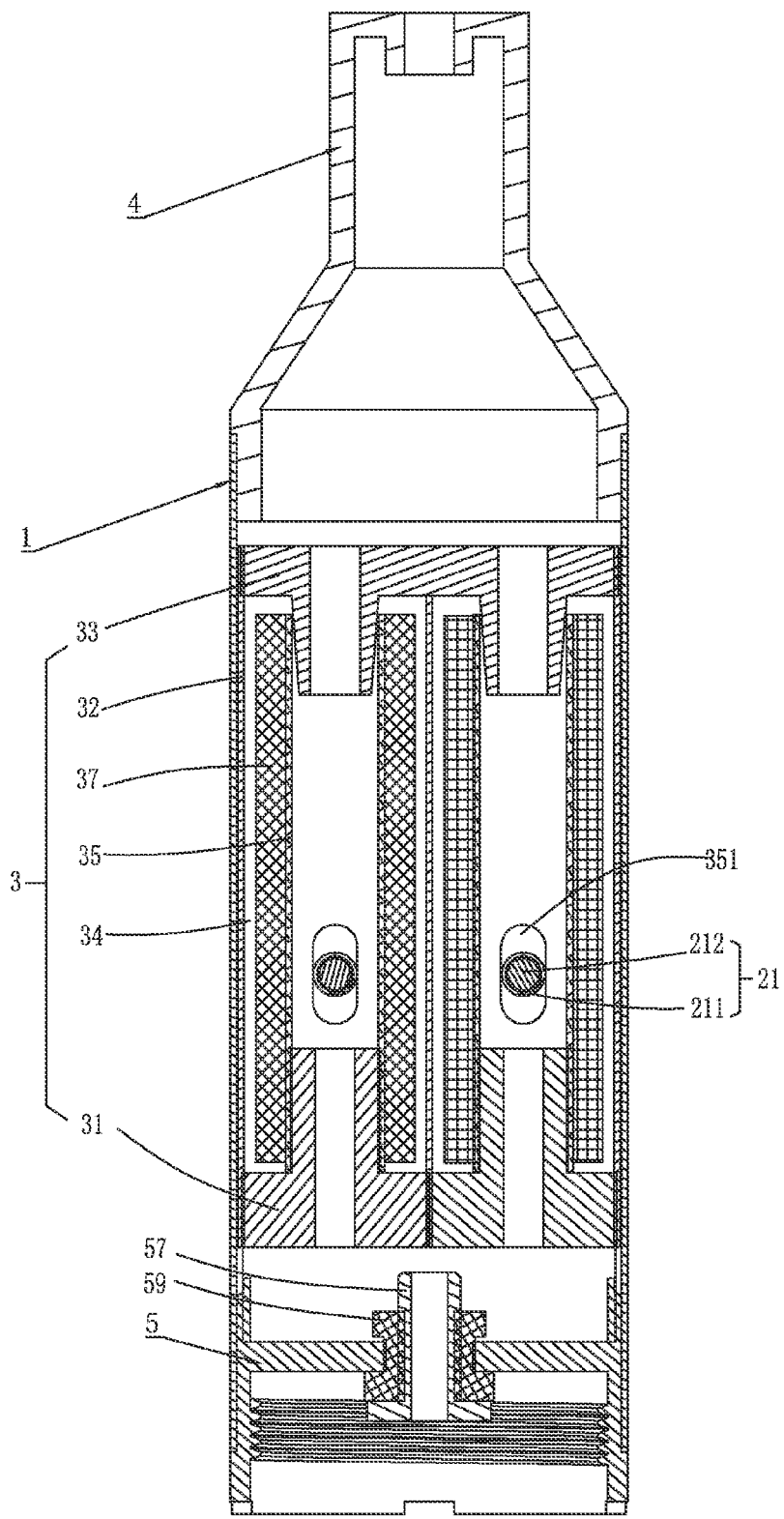
FIG. 3 is a cross-sectional view of a sucking rod of the multi-flavored electronic cigarette in accordance with the first embodiment of the present invention.

As shown in FIG. 3, the heater 21 is used for transferring the liquid smoke into smoke by atomization, and comprises a heating wire 211 and a liquid guiding component 212 used for absorbing liquid smoke and supporting the heating wire 211, the heating wire 211 are wrapped on the liquid guiding component 212, and the liquid guiding component 212 can absorb water and reserve water like sponge, and is made of glass fibers or a material having a liquid-absorbent and fluid barrier properties, such as a cotton material. In the embodiment, the liquid guiding component 212 is fixedly received within the liquid smoke cup 3, and opposite ends of the heating wire 211 are extended out of the liquid smoke cup 3 and then electrically connected with a positive electrode and a negative electrode in the power rod 91.

Figure 4:
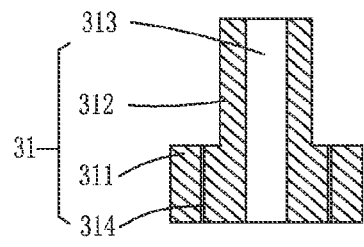
FIG. 4 is a cross-sectional view of a cup holder of the sucking rod of the multi-flavored electronic cigarette in accordance with the first embodiment of the present invention.
Figure 5:
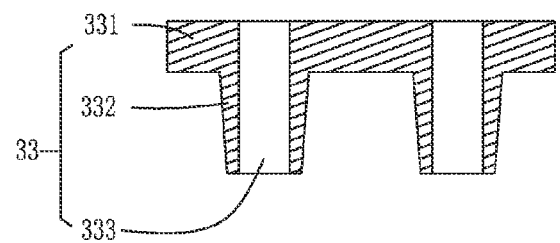
FIG. 5 is a cross-sectional view of a lid of the sucking rod of the multi-flavored electronic cigarette in accordance with the first embodiment of the present invention.
Figure 6:
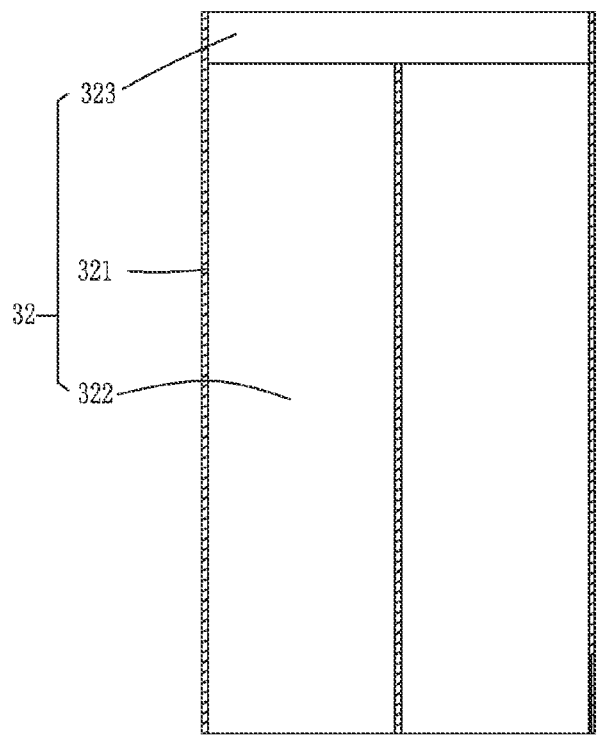
FIG. 6 is a cross-sectional view of a cup tube of the sucking rod of the multi-flavored electronic cigarette in accordance with the first embodiment of the present invention.

As shown in FIG. 3 and FIG. 4, in the embodiment, the liquid smoke cup 3 comprises two cup holders 31 each with a first venthole 313 axially therethrough, a cup tube 32 defined two atomzing chambers 34 therethrough side by side, a lid 33 with two second ventholes 333 axially therethrough each corresponding to the first venthole 313, two conduits 35 and two liquid storage components 37, the liquid smoke cup 3 is provided with the atomizing chambers 34 therein used for atomizing the liquid smoke. Wherein, the cup holders 31 and the lid 33 are disposed at opposite ends of the cup tube 32 with one of the first vent hole 313 and one of the second venthole 333 being communicated with each other through the conduit 35 and then being communicating with an exterior of the liquid smoke cup and the inner chamber of the sucking cylinder, the conduits 35 are secured in the atomizing chamber 34 side by side between the cup holder 31 and the lid 33; the liquid storage components 37 are fixed onto an exterior of the conduit 35 and disposed between the cup holder 31 and the lid 33.

The cup holder 31 (see FIG. 3 and FIG. 4) comprises a circular main body 311, a positioning post 312 axially extended from a central portion of a top surface of the main body 311 and a venthole 313 axially extended through the positioning post 312 and the main body; the cup holder 31 further forms perforations 314 for conductive wires of the heating wires 211 to pass through. The main body 311 is secured to an inner wall of a cavity 322 of the cup tube 32 described in details hereafter by means of expanding its sidewall. The cup holder 31 is capable of being made of silicone material.

The cup tube 31 (see FIG. 3 and FIG. 6) is cylindrical, and comprises cylindrical main body 321, the cavities 322 disposed within and axially parallel extended through the main body 321, and a through hole 323; the cup tube 32 forms at least two cavities 322 as the atomizing chambers 34 therein used for receiving the liquid storage components 37 and the heater 21, in the embodiment there are two cavities 322, the two cavities both are communicated with the through hole 323, and each cavity 322 reserves different flavor of liquid smoke. The main body 321 is secured to an inner wall of the sucking cylinder 1 by means of expanding its sidewall. The through hole 323 is used for mounting the lid 33.

The lid 33 (see FIG. 3 and FIG. 5) is capable of being made of silicone material, in the embodiment, it comprises a circular main body 331, two positioning posts 332 axially extended from a bottom wall of the main body 331, and two ventholes 333 axially extended through the positioning posts 332 and the main body 331, the lid 33 has its outer diameter is a little bit bigger that an inner diameter of the through hole 323 of the cup tube 32, the lid 33 is secured to an inner wall of the through hole 323 by means of expanding its sidewall. When the liquid smoke in the liquid smoke cup 3 is used out, taking out of the lid 33 can allow to add the needed liquid smoke into the atomizing chambers 34 of the liquid smile cup 3 by taking out of the lid 33. The lid 33 of the embodiment is fit for the main body 1, and forms two positioning posts 332 thereon used for engaging with the two cavities 322, the positioning posts 332 of the lid 33 correspond to the positioning posts 311 of the cup holder 31, and respectively fix opposite ends of the conduits 35. The main body 331 of the lid 33 has its bottom wall to correspond to the top wall of the main bodies 311 of the cup holder 31 and the closed inner chambers formed between the bottom wall and the sidewall of the cavities 322 are the atomizing chambers 34, the liquid storage components 37 are received in the atomizing chambers 34.

The conduit 35 (see FIG. 2 and FIG. 3) is used for supporting the liquid storage components 37 and supporting the liquid guiding component 212, and further serving as a channel for smoke generated by the liquid smoke which is atomized by the heater 21. In the embodiment, the conduit 35 is a hollow circular pipe, and capable of being made of plastic or fiber materials, such as glass fiber, which comprises a top portion and a bottom portion, the top portion is sleeved around the positioning posts 332 of the lid 33 and fittingly engaged with a circumferential wall of the positioning posts 332. The conduit 35 forms a locking slot 351 extending through the pipe wall thereof, used for supporting and fixing the liquid guiding component 212, the liquid guiding component 212 spans opposite ends of the conduit 35 and respectively passes through the locking slots 351 and abuts against the liquid storage components 37 for absorbing the liquid smoke for atomization by the heating wires 211.

The liquid storage component 37 (see FIG. 2 and FIG. 3) is used for absorbing and storing the liquid smoke injected into the liquid smoke cup 3 for facilitating a subsequent atomization by the heater 2, which can absorb water and reserve water like a sponge, and can be made of a material having a liquid-absorbent and fluid barrier properties, such as a cotton material. The liquid storage component 37 has a hollow tube structure, which is sleeved around an outer side of the conduits 35 and supported with the outer wall of the conduits 35 by mutual expansion thereof, and received in the atomizing chamber 34. The liquid storage component 37 has its sidewall to abut against the liquid guiding component 212, the liquid smoke is penetrated into and absorbed by the liquid guiding component 212 from the liquid storage component 37 and then vaporized into smoke by the heating wires 211.

As shown in FIG. 1 and FIG. 3, the first connector 5 has a shape fit with the sucking cylinder 1, which is made of conductive material, such as iron material. The first connector 5 is substantially a hollow cylinder, and comprises a cylindrical main body and a positioning flange radically outwardly extended from the main body, the main body is inserted into the sucking cylinder 1 to be positioned by means of the positioning flange and securely engaged with the sucking cylinder 1, the first connector 5 on its inner wall forms inner threads used for engaging with the second connector 6, and is further provided with a locking ring at its inner wall. In the embodiment, the first connector 5 serves as a second electrode (such as positive electrode) of the heater 21. The first connector 5 is provided with a first electrode 57 (such as negative electrode) of the heater and a first insulating sleeve 59 therein; the first electrode 57 of the heater forms a venthole at a central portion thereof, the first electrode 57 of the heater is mounted into the locking ring by means of the first insulating sleeve 59 and insulated from the first connector 5.

Figure 2:
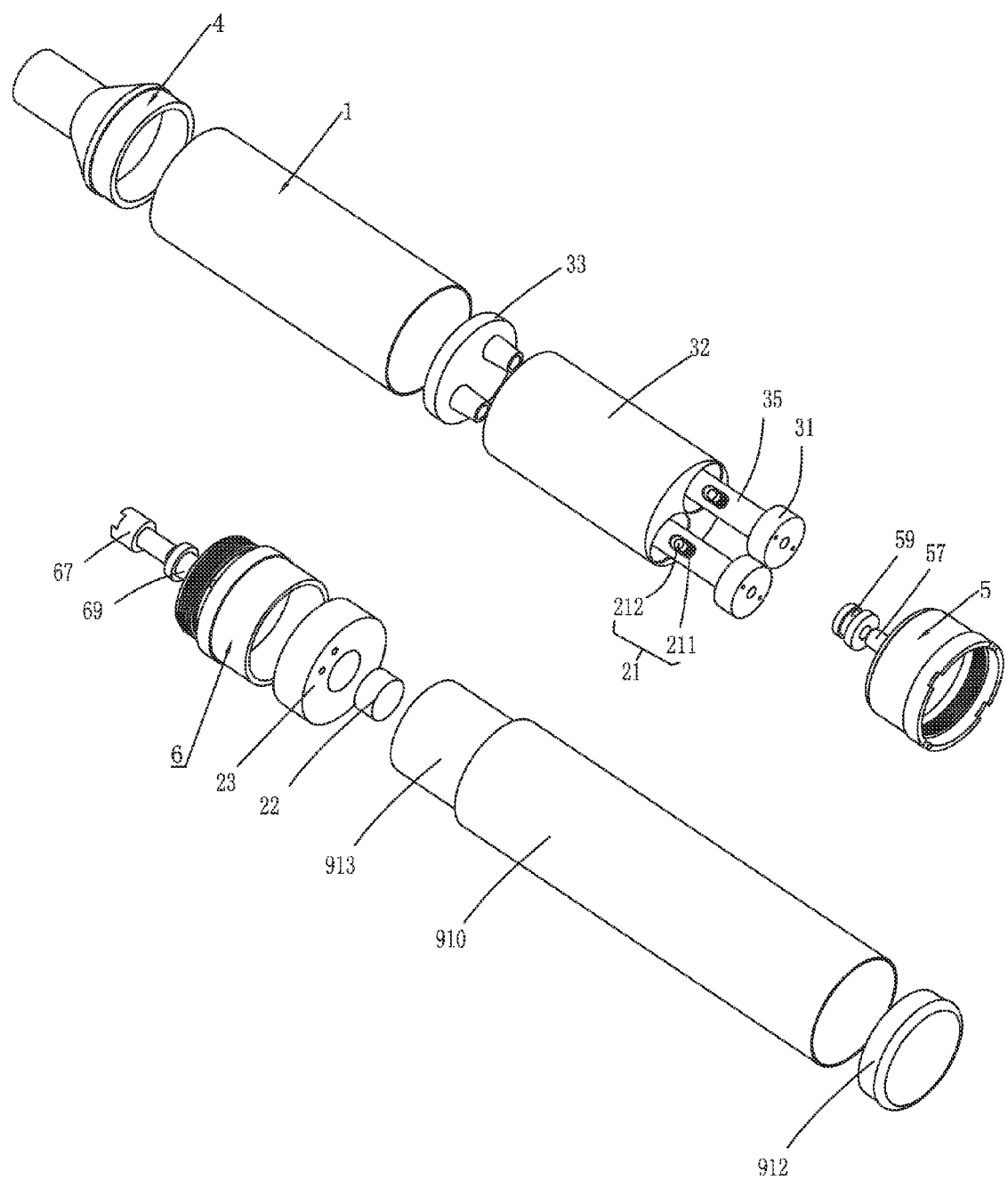
FIG. 2 is an exploded view of the multi-flavored electronic cigarette in accordance with the first embodiment of the present invention.

As shown in FIG. 2 and FIG. 3, the power rod 91 comprises a sheath 910, the second connector 6 and end cap 912 respectively disposed at opposite ends of the sheath 910, and a battery 913 received in the sheath 910.

As shown in FIG. 1 and FIG. 2, the second connector 6 and the first connector 5 are matched, the second connector 6 is disposed at a top end of the sheath 910, used for connecting the sucking cylinder 90 with the power rod 91, and is made of conductive materials, such as iron material; the second connector 6 is substantially a hollow cylinder, and comprises a cylindrical upper portion and a cylindrical lower portion, the upper portion externally forms outer threads used for threadedly engaging with the inner threads of the first connector 5, a positioning step is provided between the upper portion and the lower portion for matching with the sheath 910, the second connector 6 is secured to the inner wall of the sheath 910 by expansion of its bottom outer wall. The second connector 6 is provided with a locking ring at its inner wall. The second connector further is provided with a first electrode 67 of the battery therein used for being electrically connected to an electrode (such as negative electrode) of the battery 913 and a second insulating sleeve 69, the first electrode 67 of the battery forms a venthole in a central portion thereof, and the first electrode 67 of the battery is mounted to the locking ring of the second connector by means of the second insulating sleeve 69 and insulated from the second connector 6. In the embodiment, the second connector 6 serves as a second electrode (such as positive electrode) of the battery 913.

Each atomizing chamber 34 is provided with a liquid storage component 37 therein adapted for reserving a flavored liquid smoke, and each atomizing chamber 34 is correspondingly provided with a heater 21 therein, each heater 21 is connected to the heater control circuit board 22, and is controlled by a control switch (not shown), the control switch is disposed on an outer wall of the electronic cigarette, for starting work of the heater 21 in the atomizing chamber 34 corresponded to the required flavor of liquid smoke. Before the electronic cigarette works, a small amount of liquid smoke is penetrated from the liquid storage component 37 and stored in the liquid guiding component 212, during work, pressing the control switch corresponding to the required flavor of liquid smoke, the heater control circuit board 22 controls the heater 21 in the corresponding atomizing chamber 34 to work, the heating wire 211 is conducted and heated, to heat and atomize the liquid smoke in the liquid guiding component 212 to smoke, the smoke passes through the conduits 5 and the lid 33 to an exterior of the liquid smoke cup 3 and gets into the inner chamber of the sucking cylinder 1, and then passes through the venthole of the sucking nozzle 4 to be inhaled by smoker. Since each atomizing chamber is provided with a heater 21 to atomize the liquid smoke reserved therein, the atomized smoke in each atomizing chamber 34 gets into the inner chamber of the sucking cylinder 1, smokers can correspondingly start the heater 21 in single atomizing chamber 34 through the control switch as they like to atomize the required flavor of liquid smoke, to satisfy the requirement of optionally choosing single, multiple or any combination of several flavor(s) of smoke liquid, if multiple flavors are needed, the required flavors of liquid smoke are atomized by the heaters 21 in their own atomizing chamber 34, and then the smoke with multiple flavors are mixed in the sucking cylinder 1 and inhaled by smokers.

The electronic cigarette of the present invention, adopts two atomizing chambers 34, capable of providing two different flavors of liquid smoke for smokers to choose, certainly, also can adopt three or more atomizing chambers 34 according to client need, the amounts of other related components cooperated with the atomizing chambers 34 are adaptively adjusted. The electronic cigarette 100 in the embodiment of the present invention adopts a split-type structure, understandably, the electronic cigarette 100 can also adopt an integral structure, and the sucking cylinder and the power rod are integrally formed.

The above-mentioned is only the embodiments of the present invention. It should be noted, for the persons of ordinary skill in this field, improvements and modifications within the spirit of the present invention can be made, and the improvements and modifications should be seemed to be included in the claimed scope of this invention.

What is claimed is:

1. A multi-flavored electronic cigarette, comprising an electronic cigarette sucking rod, the cigarette sucking rod comprising a sucking cylinder with a hollow inner chamber therethrought and a liquid smoke cup disposed within the sucking cylinder; the liquid smoke cup comprising at least two cup holders each with a first venthole axially therethrough, one cup tube with at least two atomizing chambers therethrough side by side, one lid with at least two second ventholes axially therethrough each corresponding to the first venthole, at least two conduits each as a channel for smoke, at least two liquid storage components adapted for reserving liquid smoke and at least two heaters each disposed in the corresponding liquid storage component adapted for atomizing liquid smoke to smoke; the conduits are respectively secured side by side in each atomizing chamber between the cup holders and the lid; each liquid storage component has a hollow tube structure, which is sleeved around an outer side of the corresponding conduit; the liquid storage components are made of high temperature resistant cotton, fiberglass cotton or thick cotton cloth capable of absorbing water and reserving water like a sponge; the cup holders and the lid are disposed at opposite ends of the cup tube with one of the first vent hole and the corresponding second venthole being communicated with each other through the conduit and then being communicating with an exterior of the liquid smoke cup and the inner chamber of the sucking cylinder; each of the at least two atomizing chambers are adapted for allowing a kind of liquid smoke to be atomized therein to become smoke; one liquid storage component with a flavored liquid smoke therein and one heater are provided in each atomizing chamber, the electronic cigarette being further provided with a heater control circuit board therein electrically connected with each heater, a battery electrically connected with the heater control circuit board and a control switch disposed on an outer shell of the electronic cigarette.

2. The multi-flavored electronic cigarette as described in claim 1, wherein, the atomizing chambers each are provided with one conduit adapted for supporting the liquid storage components, the liquid storage components are sleeve-shaped, and sleeved around outer portions of the conduits.

3. The multi-flavored electronic cigarette as described in claim 2, wherein, the heaters each comprise a heating wire and a liquid guiding component adapted for absorbing liquid smoke and supporting the heating wire, the conduits each form a locking slot extending through a side wall thereof in a radial direction and adapted for mounting the liquid guiding component, opposite ends of the liquid guiding component project the side wall of the conduits and abut against inner sides of the liquid storage components.

4. The multi-flavored electronic cigarette as described in claim 3, wherein, the liquid guiding component is made of glass fiber which is capable of absorbing water and reserving water like a sponge or a material having a liquid-absorbent and fluid barrier properties.

5. The multi-flavored electronic cigarette as described in claim 3, wherein, the sucking cylinder is further provided with a liquid smoke cup configured for receiving the liquid storage components and the heaters, the at least two atomizing chambers are disposed in the liquid smoke cup.

6. The multi-flavored electronic cigarette as described in claim 5, wherein, the cup tube is adapted with the inner side of the sucking cylinder, the cup tube is provided with at least two cavities, the lid is inserted into a top end of the cup tube and hermetically connected with a circumference of the top end of the cavities, the cup holders are inserted into a bottom end of the cup tube and hermetically connected with a circumference of the bottom end of the cavities, the lid and the cup holders are corresponded to restrain the opposite ends of the conduit, the lid and the cup holders are corresponded and construct sealed inner chambers served as the atomizing chambers together with side walls of the cavities, the liquid storage component is disposed within the atomizing chambers.

7. The multi-flavored electronic cigarette as described in claim 6, wherein, the cavities are cylinder-shaped, the lid comprises a circular main body, positioning posts axially extended from a bottom wall of the main body to restrain the conduits and the second ventholes axially extended through the position posts and the main body of the lid; correspondingly, the cup holders each comprise a circular main body, a positioning post axially extended from a central portion of a top wall of the main body of the corresponding cup holder to restrain the conduits and the first venthole axially extended through the positioning post and the main body of the corresponding cup holder; the positioning posts of the lid and the positioning posts of the cup holders are respectively inserted into opposite ends of the conduits to position the conduits in the atomizing chambers.

8. The multi-flavored electronic cigarette as described in claim 6, wherein, the electronic cigarette adopts a split-type structure, and comprises mutually connected sucking rod and a power rod, the sucking rod at its one end is provided with a first connector, correspondingly, the power rod at its one end is provided with a second connector securely engaged with the first connector.

9. The multi-flavored electronic cigarette as described in claim 8, wherein, the heater and the liquid smoke cup are disposed within the sucking rod, while the battery and the heater control circuit board are disposed within the power rod; the first connector is provided with a first electrode of the heater and a first insulating sleeve therein, the first electrode of the heater is mounted by means of the first insulating sleeve into the first connector which serves as a second electrode of the heater; the second connector is provided with a first electrode of the battery and a second insulating sleeve therein; the first electrode of the battery is mounted by means of the second insulating sleeve into the second connector which serves as a second electrode of the battery.

10. The multi-flavored electronic cigarette as described in claim 6, wherein, the sucking rod and the power rod are connected by fastener, plug or screw.

11. The multi-flavored electronic cigarette as described in claim 6, wherein, the electrode cigarette is integrally formed.

12. The multi-flavored electronic cigarette as described in claim 1, the electronic cigarette sucking rod further comprising a sucking nozzle with a third venthole for the smoker inhaling; the sucking nozzle is mounted to an end of the sucking cylinder with the third venthole being communicated with the inner chamber of the sucking cylinder.

13. An electronic cigarette sucking rod, comprising a sucking cylinder with a hollow inner chamber, and a sucking nozzle mounted to one tip end of the sucking cylinder; the sucking nozzle has a third venthole communicated with the hollow inner chamber of the sucking cylinder for smoker inhaling; a cylindrical cup tube is axially disposed in sucking cylinder; the cylindrical cup therein radially defines at least two cavities therethrough side by side, and a through hole above and communicated with the cavities; each cavities receives a liquid storage components with a hollow tube structure; liquid smoke is absorbed and stored in the liquid storage component, a conduit as a channel for smoke is coaxially and tightly supported in the liquid storage component; each conduit is provided with a heater therein to atomize the liquid smoke from the corresponding liquid storage component into smoke; a lid defined at least two second ventholes side by side therethrough is fittingly engaged in one end of the cup tube for covering each top end of each cavity; at least two cup holders each axially defined a first venthole therethrough; each cup holder is disposed at the other end of the cup tube for covering a bottom end of each corresponding cavity; each first vent hole and one of the corresponding second venthole being communicated with each other through the conduit and then being communicating with an exterior of the liquid smoke cup and the inner chamber of the sucking cylinder.

* * * * *